(12) United States Patent
Heller et al.

(10) Patent No.: US 7,668,592 B2
(45) Date of Patent: Feb. 23, 2010

(54) ELECTROPORATION AND ELECTROPHORESIS SYSTEM AND METHOD FOR ACHIEVING MOLECULAR PENETRATION INTO CELLS IN VIVO

(75) Inventors: Richard Heller, Temple Terrace, FL (US); Richard Gilbert, Tampa, FL (US); Mark J. Jaroszeski, Tampa, FL (US); Loree C. Heller, Temple Terrace, FL (US); Melinda L. Lucas, Tampa, FL (US)

(73) Assignee: University of South Florida, Tampa, FL (US)

( * ) Notice: Subject to any disclaimer, the term of this patent is extended or adjusted under 35 U.S.C. 154(b) by 2 days.

(21) Appl. No.: 11/781,619

(22) Filed: Jul. 23, 2007

(65) Prior Publication Data

US 2008/0033340 A1    Feb. 7, 2008

Related U.S. Application Data

(62) Division of application No. 10/708,111, filed on Feb. 10, 2004, now abandoned, which is a division of application No. 09/507,859, filed on Feb. 22, 2000, now Pat. No. 6,714,816.

(51) Int. Cl.
  *A61N 1/30* (2006.01)
(52) U.S. Cl. ........................................ 604/20
(58) Field of Classification Search .......... 604/20; 607/1, 2, 3
  See application file for complete search history.

(56) References Cited

U.S. PATENT DOCUMENTS

| | | | |
|---|---|---|---|
| 5,019,034 A | 5/1991 | Weaver et al. | |
| 5,071,536 A | 12/1991 | Ivory | |
| 5,108,567 A | 4/1992 | Kolble | |
| 5,389,069 A | 2/1995 | Weaver | |
| 5,551,953 A | 9/1996 | Lattin et al. | |
| 5,720,921 A | 2/1998 | Meserol | |

(Continued)

FOREIGN PATENT DOCUMENTS

WO    99/62592    12/1999

(Continued)

OTHER PUBLICATIONS

Joshi and Shoenbach, "Electroporation dynamics in biological cells subjected to ultrafast electrical pulses: A numerical simulation study", Jul. 2000, The American Physical Society, vol. 62, No. 1, pp. 1025-1033.*

(Continued)

*Primary Examiner*—Nicholas D Lucchesi
*Assistant Examiner*—Theodore J Stigell
(74) *Attorney, Agent, or Firm*—Molly L. Sauter; Smith & Hopen, P.A.

(57) ABSTRACT

The electroporation system and method combine pulses having different characteristics for delivering molecules to cells in vivo. The pulses include a high-intensity pulse for inducing electroporation and a low-intensity pulse to induce electrophoretic molecule movement within an interstitial space, molecule adherence to a cell membrane, and electrophoretic movement of the molecule through the permeabilized membrane. The use of a high-intensity and a low-intensity pulse achieves improved delivery; reduction of intensity and/or duration of pulses for inducing electroporation; and decreased muscle stimulation, tissue damage, and patient discomfort.

12 Claims, 13 Drawing Sheets

U.S. PATENT DOCUMENTS

| | | |
|---|---|---|
| 5,869,326 A | 2/1999 | Hofmann |
| 5,873,849 A | 2/1999 | Bernard |
| 5,911,223 A | 6/1999 | Weaver et al. |
| 5,968,006 A | 10/1999 | Hoffmann |
| 6,117,660 A | 9/2000 | Walters et al. |
| 6,135,990 A * | 10/2000 | Heller et al. ............ 604/500 |
| 6,314,316 B1 | 11/2001 | Heller et al. |
| 2004/0104669 A1 | 6/2004 | Takeuchiet et al. |

FOREIGN PATENT DOCUMENTS

| | | |
|---|---|---|
| WO | 00/35532 | 6/2000 |

OTHER PUBLICATIONS

Heller et al., FEBS Lett. 389, 225-228, In vivo gene electroinjection and expression in rat liver.

* cited by examiner

Prior Art

ELECTROPORATION AND ELECTROPHORESIS SYSTEM AND METHOD FOR ACHIEVING MOLECULAR PENETRATION INTO CELLS IN VIVO

CROSS-REFERENCE TO RELATED APPLICATIONS

This application is a divisional application of patent application Ser. No. 10/708,111 of the same title by the same inventor, filed Feb. 10, 2004 and now abandoned, which is a divisional application of patent application Ser. No. 09/507,859 filed Feb. 22, 2000 now issued U.S. Pat. No. 6,714,816.

FIELD OF INVENTION

The present invention relates to methods and apparatus for delivering molecules into a target cell, and, more particularly, to such methods and apparatus for achieving such delivery into cells in vivo through electroporation and electrophoresis.

BACKGROUND OF THE INVENTION

The effect of electromagnetic fields on cell membranes has been studied since the 1960s. Early research focused on describing observations that an applied electric field can reversibly break down cell membranes in vitro. Throughout the 1970s the topic was more common in the literature and continued to focus on describing the phenomenon that resulted from brief exposure to intense electric fields as well as the entry of exogenous molecules to the cell interior as a result of membrane breakdown. Applications began to emerge along with a better understanding of reversible membrane breakdown in the 1980s.

Prior research led to the current understanding that exposure of cells to intense electric fields for brief periods of time temporarily destabilized membranes. This effect has been described as a dielectric breakdown due to an induced transmembrane potential, and was termed "electroporation," or "electropermeabilization," because it was observed that molecules that do not normally pass through the membrane gain intracellular access after the cells were treated with electric fields. The porated state was noted to be temporary. Typically, cells remain in a destabilized state on the order of minutes after electrical treatment ceases.

The physical nature of electroporation makes it universally applicable. A variety of procedures utilize this type of treatment, which gives temporary access to the cytosol. These include production on monoclonal antibodies, cell-cell fusion, cell-tissue fusion, insertion of membrane proteins, and genetic transformation. In addition, dyes and fluorescent molecules have been used to investigate the phenomenon of electroporation. A notable example of loading molecules into cells in vivo is electrochemotherapy. The procedure utilizes a drug combined with electric pulses as a means for loading tumor cells with an anticancer drug, and has been performed in a number of animal models and in clinical trials by the present inventors. Also, plasmid DNA has been loaded into rat liver cells in vivo (Heller et al., *FEBS Lett.* 389, 225-28). The methods published thus far for all in vivo applications utilize multiple direct current pulses that are substantially identical (single amplitude, single pulse duration, and a single duty cycle for delivery). It is known that temporary permeabilization of cell membranes can result if the effects of pulsation fall within two thresholds. First, the intensity of the applied pulses must be above a threshold value in order to electropermeabilize the membranes. This value is cell-type dependent. Second, if the intensity of the treatment is too high, then cells will be killed as a result of membrane damage, which can negate any desired effect of a molecule introduced into the cell. Thus it is critical to apply pulses with intensities that are above the described lower threshold but below the upper threshold in order to impart a temporary permeabilized state.

Protocols for the use of electroporation to load cells in vitro typically use a suspension of single cells or cells that are attached in a planar manner to a growth surface. In vivo electroporation is more complex because tissues are involved. Tissues are composed of individual cells that collectively make up a three-dimensional structure. In either case, the effects on the cell are the same.

FIGS. 1A-1E illustrate details of the electrical treatment procedure. The method comprises:

1. A living biological cell in an electrically conductive medium is positioned between two electrodes (FIG. 1A). The cell's resting transmembrane potential is indicated by + and − signs to indicate the separated ionic species that make up the potential.

2. Application of an electrical field (in the form of an applied potential +V) between the two electrodes causes accumulation of charge on either side of the cell. The separated charge adds to the resting potential, resulting in an overall transmembrane potential (resting plus induced). This charge will accumulate as the applied field is increased up to a critical threshold value that is cell-type dependent.

3. If the overall transmembrane potential is increased above this threshold, by applying a field with sufficient magnitude indicated by the pulse +V (FIG. 1C), then the cell membrane is dielectrically broken down. This membrane breakdown has been termed electroporation and/or electropermeabilization. Cells electroporate preferentially in the membrane region that faces the +electrode as the accumulation of charge in this membrane region adds directly to the resting potential. Less poration takes place in the opposite side of the cell because the accumulation of induced charge first cancels the resting potential and then accumulates locally to form an induced potential. Thus a lower total transmembrane potential is induced on this side of the cell, which results in a lower degree of poration.

4. Immediately after electroporation, there is a rapid depolarization of the membrane that takes place as a result of the aqueous electropores (FIG. 1D).

5. Normal membrane fluidity allows the electropores to seal in a time frame that is approximately on the order of minutes (FIG. 1E).

The loading of molecules by electroporation in vitro as well as in vivo is typically carried out by first exposing the cells or tissue of interest to a drug or other molecule (FIG. 2A). The cells or tissue are then exposed to electric fields by administering one or more direct current pulses (FIG. 2B). Electrical treatment is conducted in a manner that results in a temporary membrane destabilization with minimal cytotoxicity. The intensity of electrical treatment is typically described by the magnitude of the applied electric field. This field is defined as the voltage applied to the electrodes divided by the distance between the electrodes. Electric field strengths ranging from 100 to 5000 V/cm have been successfully used, as reported in the literature, for delivering molecules in vivo and are also specific to the cells or tissue under investigation. Following cessation of stimulation, the pores reseal, with the desired molecules inside the cell (FIG. 2C).

Pulses are usually rectangular in shape; however, exponentially decaying pulses have also been used. The duration of each pulse is called pulse width. Molecule loading has been performed with pulse widths ranging from microseconds (μs) to milliseconds (ms). The number of pulses delivered has ranged from one to eight. Typically, multiple identical pulses of the order of microseconds in duration are utilized during electrical treatment.

For molecules to be delivered to the cell interior by electroporation, it is critical that the molecule of interest be near the exterior of the cell membrane at the time of electroporation. It is also critical to have molecules near all cells within a treated tissue volume in order to provide efficient delivery to all cells within the treatment volume. Currently, molecules are injected intravenously, intraarterially, directly into the treatment site to provide a supply of molecules in the extracellular spaces of the tissues for delivery into the intracellular spaces by electroporation. Other methods for introducing the molecules into the extracellular spaces of tissues such as jet injection and particle bombardment can be used to provide a source of molecules in the extracellular space for delivery using electrical fields.

Currently known delivery methods utilize the electrode systems outlined previously using one or more pulses that are substantially identical with respect to their intensity (V/cm), pulse width, and duty cycle (if more than one pulse). Although protocols that used these types of electrodes and pulses to deliver molecules in vivo have been successful, there are some drawbacks. Pulsing protocols for delivering small molecules such as drugs, in particular, chemotherapeutic agents, have used fields in the range of 1000-5000 V/cm. Such a high-intensity field can cause patient discomfort in the form of pain and/or involuntary muscle movement. Such drug-delivery protocols typically use multiple pulses on the order of microseconds in duration.

There are two types of pulsing protocols that have been used for delivering DNA. The first type is identical to those pulsing protocols used to deliver drugs and suffers from the same patient-related drawbacks. The second type uses pulses on the order of 100-800 V/cm, with pulses lasting up to hundreds of milliseconds. The drawback of these pulses is that their duration can cause great discomfort and also tissue damage.

SUMMARY OF INVENTION

It is therefore an object of the present invention to provide an improved system and method for delivering molecules to cells in vivo.

It is an additional object to provide such a system and method that do not produce the discomfort and tissue damage associated with previously used devices and methods.

These objects and others are achieved by the system and method of the present invention, which combine pulses having different characteristics delivering molecules to cells in vivo. The pulses of the present invention comprise a high-intensity pulse for inducing electroporation and a low-intensity pulse to induce electrophoretic molecule movement within an interstitial space, molecule adherence to a cell membrane, and electrophoretic movement of the molecule through the permeabilized membrane.

The molecules, which may comprise a unitary charged molecule or a plurality of different charged molecules, may be delivered by a method known in the art, such as by injection combined with electroporation, particle bombardment, and jet injection, although these methods are not intended as limitations. The types of molecules may include, but are not intended to be limited to, amino acids, bioactive molecules, polypeptides, proteins, antibodies (or fractions thereof), glycoproteins, enzymes, nucleic acids, oligonucleotides, RNA, DNA, competent DNA, plasmid DNA, chromosomes, drugs, other charged organic or inorganic molecules that may or may not have a localized charge region.

The use of a high-intensity and a low-intensity pulse achieves:

1. Equal or better in vivo delivery over conventional pulsing protocols using a single type of pulse.
2. Reduction of intensity and/or duration of pulses for inducing electroporation over conventional pulsing protocols using only high-intensity pulses.
3. Decreased muscle stimulation, tissue damage, and patient discomfort. Target tissue may include, but is not intended to be limited to, normal or abnormal cells within tissues, skin, tumor tissue, or muscle.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

BRIEF DESCRIPTION OF THE DRAWINGS

For a fuller understanding of the invention, reference should be made to the following detailed description, taken in connection with the accompanying drawings, in which:

FIG. 2 (prior art) The process of delivering molecules by electroporation.

DETAILED DESCRIPTION OF THE PREFERRED EMBODIMENT

A description of the preferred embodiments of the present invention will now be presented with reference to FIGS. 3-13E.

Figure 1A:
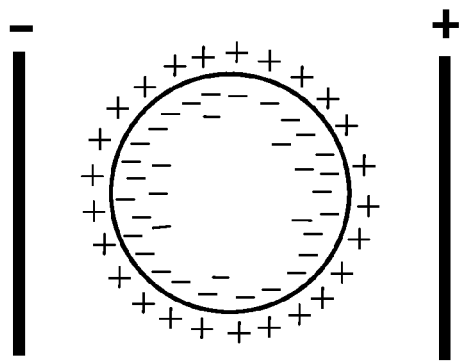
FIG. 1A-1E (prior art) Conceptual two-dimensional depiction of electroporation of a cell subjected to an electromagnetic field. Regions of membrane breakdown, depicted as pores, are formed at the ends of cells facing the electrodes. Electromagnetic field exposure is achieved by applying a potential between electrodes − and +.
Figure 1B:
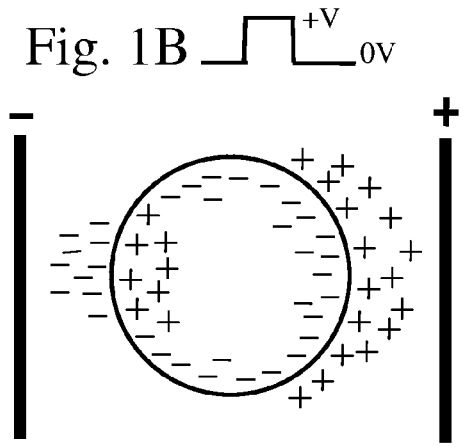
Figure 1C:
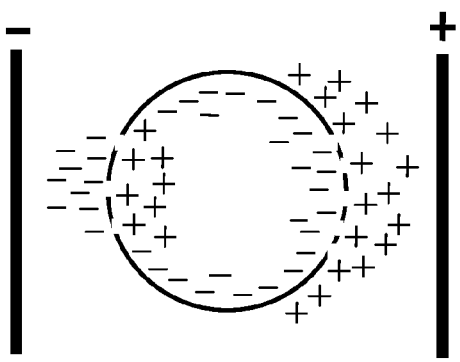
Figure 1D:
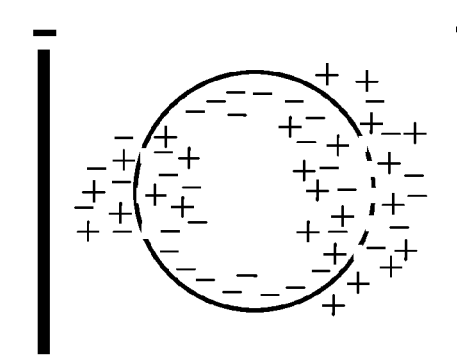
Figure 1E:
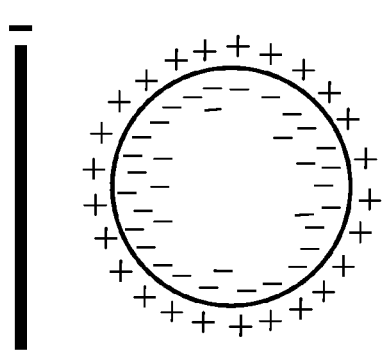
Figure 2A:
FIG. 2A. Cells in vitro or in vivo are exposed to the molecule of interest.
Figure 2A:
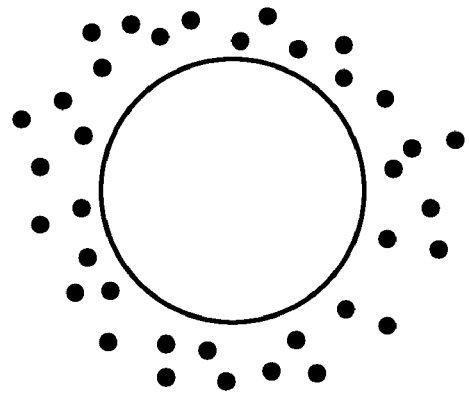
Figure 2B:
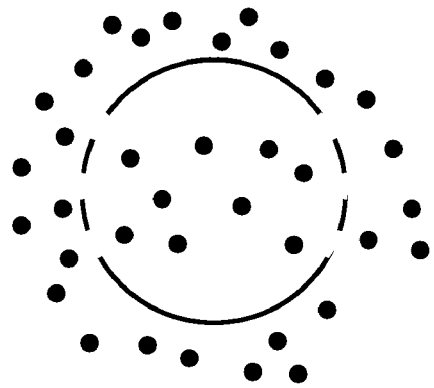
FIG. 2B. Direct current pulses are administered to the cells to cause a temporary membrane destabilization that allows the molecules to more freely enter the cell interior.
Figure 2C:
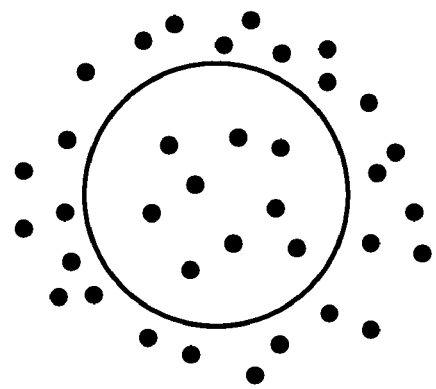
FIG. 2C. Cells return to their normal state after pulsation, leaving the molecule within the cells.
Figure 3:
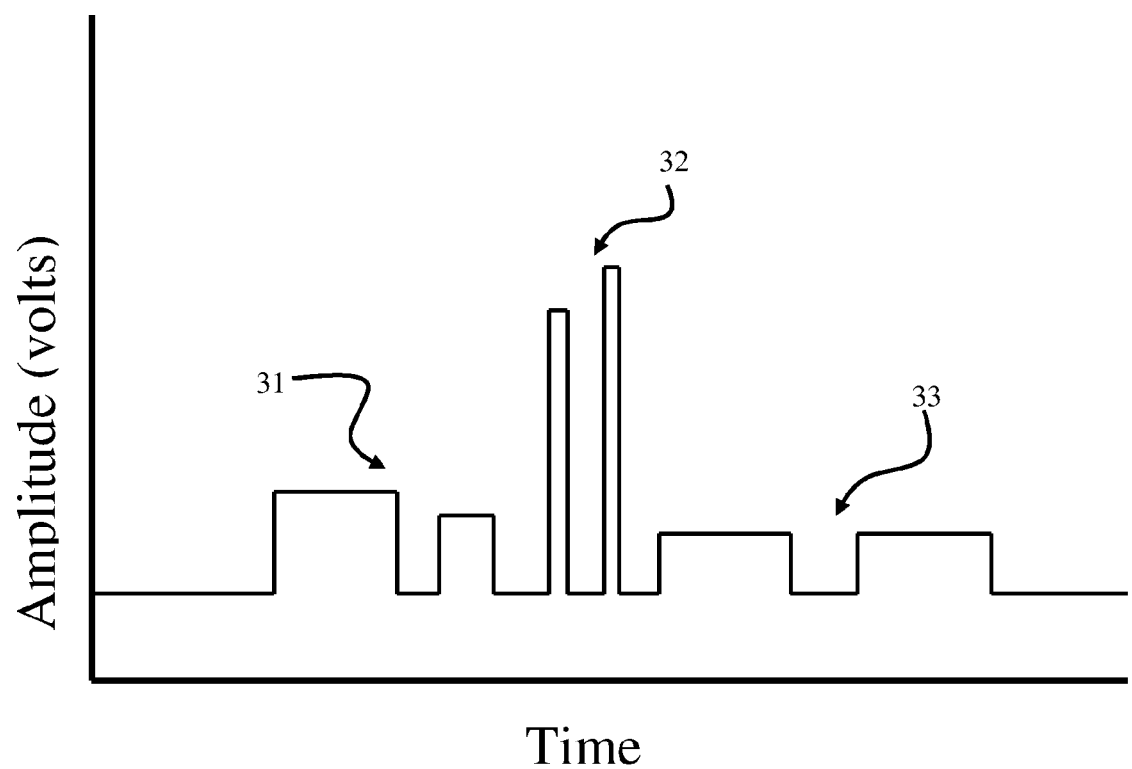
FIG. 3 is a schematic diagram of an exemplary pulsing sequence for achieving the delivery of molecules into cells in vivo.

A schematic diagram of an exemplary pulse sequence is illustrated in FIG. 3. An exemplary device for delivering pulses comprises a commercial device for producing dc pulses with characteristics needed as described herein (CytoPulse PA-4000, CytoPulse Sciences, Hanover, MD). The term field strength is used herein to indicate voltage, as is understood by those of skill in the art. Field strength is the voltage applied to the cells/tissue divided by the distance between the electrodes. The duration of each pulse, the time interval between pulses, and the number of pulses are all variables in the pulse sequence of the present invention. While the waveforms shown in FIG. 3 are dipicted as rectangular, this pulse shape is not intended as a limitation, as other waveforms can also be used. For example, at least one of the first and the second pulse may be selected from the group consisting of a rectangular direct current pulse, an alternating current pulse, a pulsed alternating current pulse, an alternating current pulse having variable frequency and amplitude, a variable direct current waveform, a variable alternating current pulse biased with constant direct current, a pulse having a triangular waveform, a pulse having exponentially rising component, and a pulse having an exponentially decaying component.

A typical sequence for practicing the present invention comprises the steps of:

1. Deliver desired molecules into the target tissue into an interstitial space by a method such as is known in the art, including one or a combination of local injection, intratissue injection, systemic injection, intravenous injection, intraarterial injection, particle 10 bombardment, and jet injection.

2. Apply two or more suitable electrodes to a segment of or the entire tissue.

3. Apply at least one low-intensity pulse having an intensity insufficient to cause membrane breakdown but sufficient to induce an electrophoretic migration of molecules within the interstitial tissue space (shown as two pulses labeled 31 in FIG. 3): This pulse can also force charged molecules to adhere to cell membranes. Pulse duration may be in the range of microseconds to seconds, or multiple serially administered pulses can be provided, their sum comprising the desired pulse duration. Field strength for this pulse is dependent upon the cell/tissue type but can range from 0 to 2000 V/cm.

4. After sufficient electrically facilitated movement within the interstitial space and/or molecule adherence to the target cells, one or more electric pulses having characteristics causing a temporary breakdown of the cell membrane are applied to the tissue/cells via the electrodes (shown as two pulses labeled 32 in FIG. 3). Although the exact characteristics of the pulses vary with cell/tissue type, pulses with field strengths in the range of 50-10,000 V/cm with pulse durations ranging from 1 μs to seconds are required for cell permeabilization. In relative terms, pulses that induce electroporation have a higher field strength than those used in (3) above. An administration of these pulses forms pathways in the membrane through which extracellular molecules can enter the cytosol.

5. Delivery can be further enhanced by molecule movement after (4) because cells that have been treated as in (4) remain in a permeabilized state for times on the order of minutes to an hour. Molecular movement can be induced electrophoretically by applying pulses that have characteristics similar to but not necessarily identical to those in (3), where, as was described, the pulse(s) can comprise a sum of multiple shorter pulses (shown as two pulses labeled 33 in FIG. 3). This increase in the quantity of molecules internalized by the cells presumably results from an electrophoretic movement of molecules from the extracellular space through the permeabilized cell membrane and into the cell interior.

The above-listed steps comprise a typical scenario including pulses having different characteristics for three basic functions:

A first type of pulse is used as in (3) to cause electrophoretic migration of a molecule within a tissue interstitial space and/or molecule adherence to a target cell. A second type of pulse is used as in (4) to cause electropermeabilization of a target cell membrane. A third type of pulse is used as in (5) to cause electrophoretic molecular movement from the extracellular space into the cell interior.

The system of the present invention may be used as follows:

1. Use electrophoresis pulses to cause molecular movement and/or molecule adherence followed by electroporation pulses only (type 1 and type 2 pulses).

2. Use electroporation pulses followed by electrophoresis pulses to move molecules into electroporated cells only (type 2 and type 3 pulses).

3. Use electrophoresis pulses only to move and/or distribute molecules throughout the tissue (type 1 pulses).

4. Move/distribute/deliver more than one type of molecule simultaneously (any combination of types 1, 2, and 3 pulses).

5. Use electric pulsing protocols as described herein to move and/or deliver two or more types of molecules that chemically react in vivo. Such a reaction can occur within the extracellular space or in the intracellular space (any combination of types 1, 2, and 3 pulses).

6. Use types of pulses other than rectangular direct current, such as alternating current, pulsed alternating current, high- and low-voltage alternating current with variable frequency and amplitude, variable direct current waveforms, variable alternating current signals biased with variable direct current waveforms, variable alternating current signals biased with constant direct current. Use alternate waveform shapes such as triangular, sawtooth, exponentially rising, exponentially decaying, etc., as can be conceived by one of skill in the art.

7. Move, distribute, and deliver molecules using the pulsing scenarios described herein such as amino acids, bioactive molecules, polypeptides, proteins, antibodies (or fractions thereof), glycoproteins, enzymes, nucleic acids, oligonucleotides, RNA, DNA, competent DNA, plasmid DNA, chromosomes, drugs, other organic and inorganic molecules that have a localized charge region, other organic and inorganic molecules that do not contain a localized charged region, and any molecule modified to contain a charged region.

Combined Use of Type 2 and Type 3 Pulses

Figure 4:
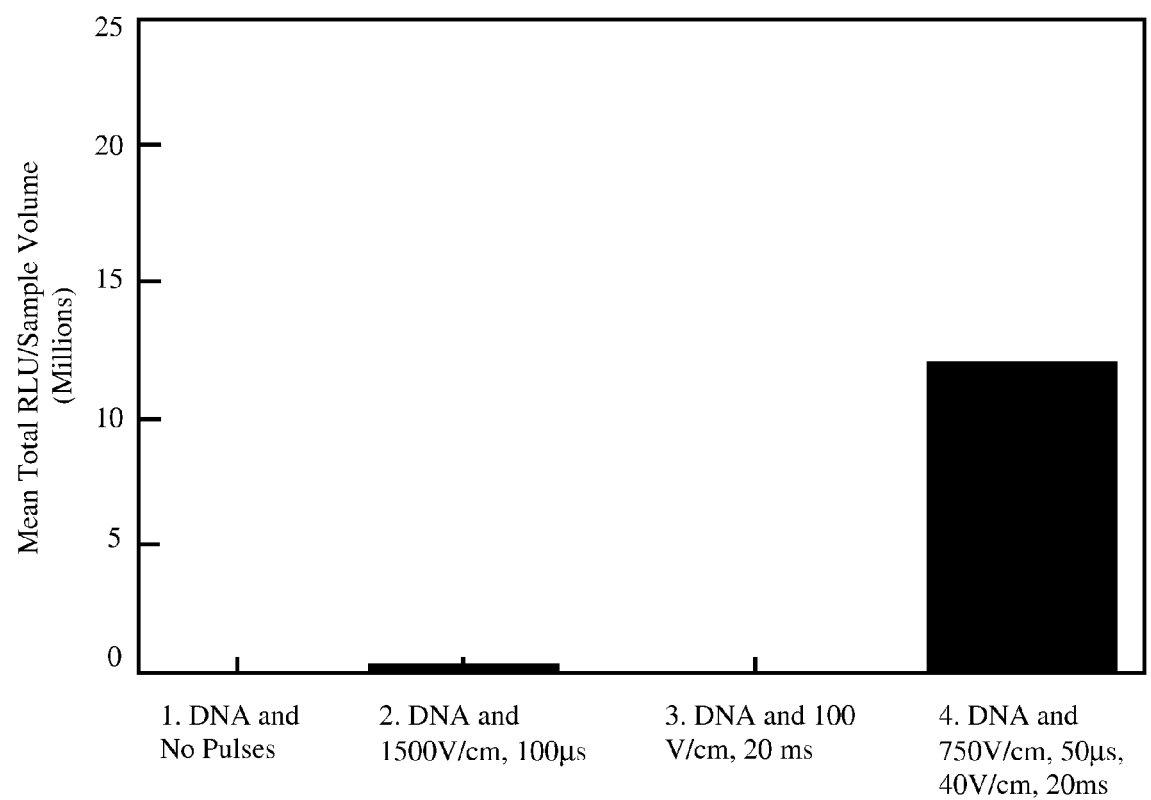
FIG. 4 shows mean quantitative expression data for luciferase in normal murine skin following application of a control and three different sequences of pulsed fields.

Mean quantitative expression data for luciferase in normal murine skin 2 days after delivery of a plasmid coding for luciferase cDNA using pulsed electric fields are shown in FIG. 4. The data indicate skin samples that were treated in four different ways, having received an intradermal injection of DNA.

1. DNA followed by no pulses.
2. DNA followed by pulses that were 1500 V/cm and 100 µs in duration (type 2 pulses).
3. DNA followed by pulses that were 100 V/cm and 20 ms in duration (type 3 pulses).
4. DNA followed by 750 V/cm pulses that were 50 µs in duration and 40 V/cm pulses that were 20 ms in duration (combined type 2 and type 3 pulses).

Method (4) achieved very high expression, while very little expression was obtained in samples treated with 1500 or 100 V/cm pulses (or no pulses). This example indicates the efficacy of using two different types of pulses, with higher expression than obtained for the sum of separately administered type 2 and type 3 pulses, even though the type 2 pulse in (4) had a lower field strength and duration (750 V/cm, 50 µs) than the type 2 pulses used alone (1500 V/cm, 100 µs). Also, the type 3 pulses used in the combined treatment (40 V/cm) provided less electrophoretic driving force than the type 3 pulses used alone (100 V/cm).

Figure 5A:
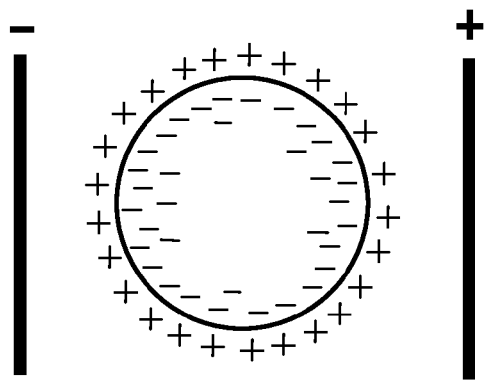
FIGS. 5A-5E illustrate a possible sequence of events leading to the synergistic effect of combining type 2 and type 3 pulses.
Figure 5B:
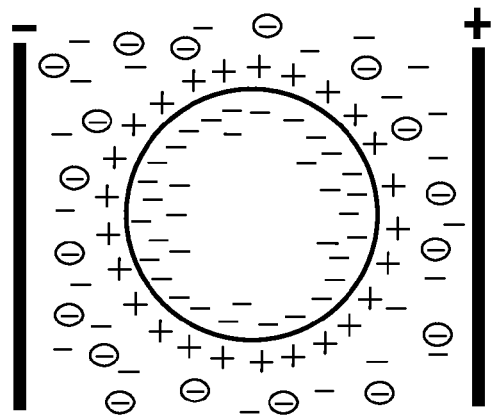

A possible explanation for this synergistic effect may be as follows and as illustrated by FIGS. 5A-5E, although this is not intended as a limitation: A cell with a resting potential in a conductive medium is positioned between two electrodes (FIG. 5A). A molecule is introduced into the tissue (plasmid DNA, for example, is negatively charged in solution; FIG. 5B).

Figure 5C:
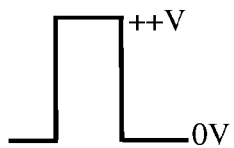

Type 2 pulses are then applied to the cells to induce electroporation (FIG. 5C). A rapid depolarization of the cell membrane results, causing an exchange of molecules on either side of the membrane.

Figure 5D:
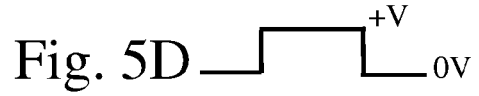
Figure 5B:
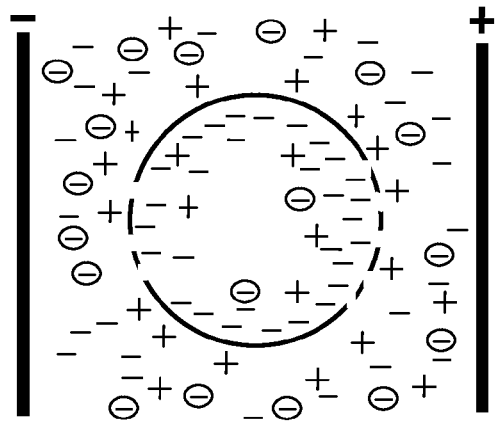
Figure 5B:
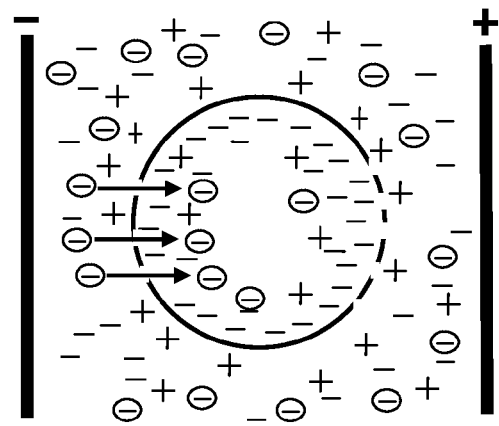
Figure 5E:
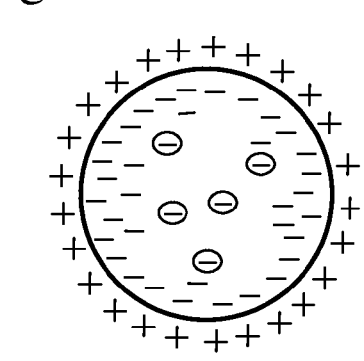

Next type 3 pulses are applied to electrophoretically drive the negatively charged plasmid DNA molecules into the electroporated cells, with the migration toward the positively charged electrode (FIG. 5D). Thus the addition of type 3 pulses may serve to enhance expression by electrophoretically moving more plasmid DNA into cells during delivery. Minutes to hours after pulsation, the cell membrane reseals by normal membrane fluidity, leaving the plasmid DNA inside the cell (FIG. 5E).

Combined Use of Type 2 and Type 3 Pulses and of Types 1, 2, and 3 Pulses

Figure 6:
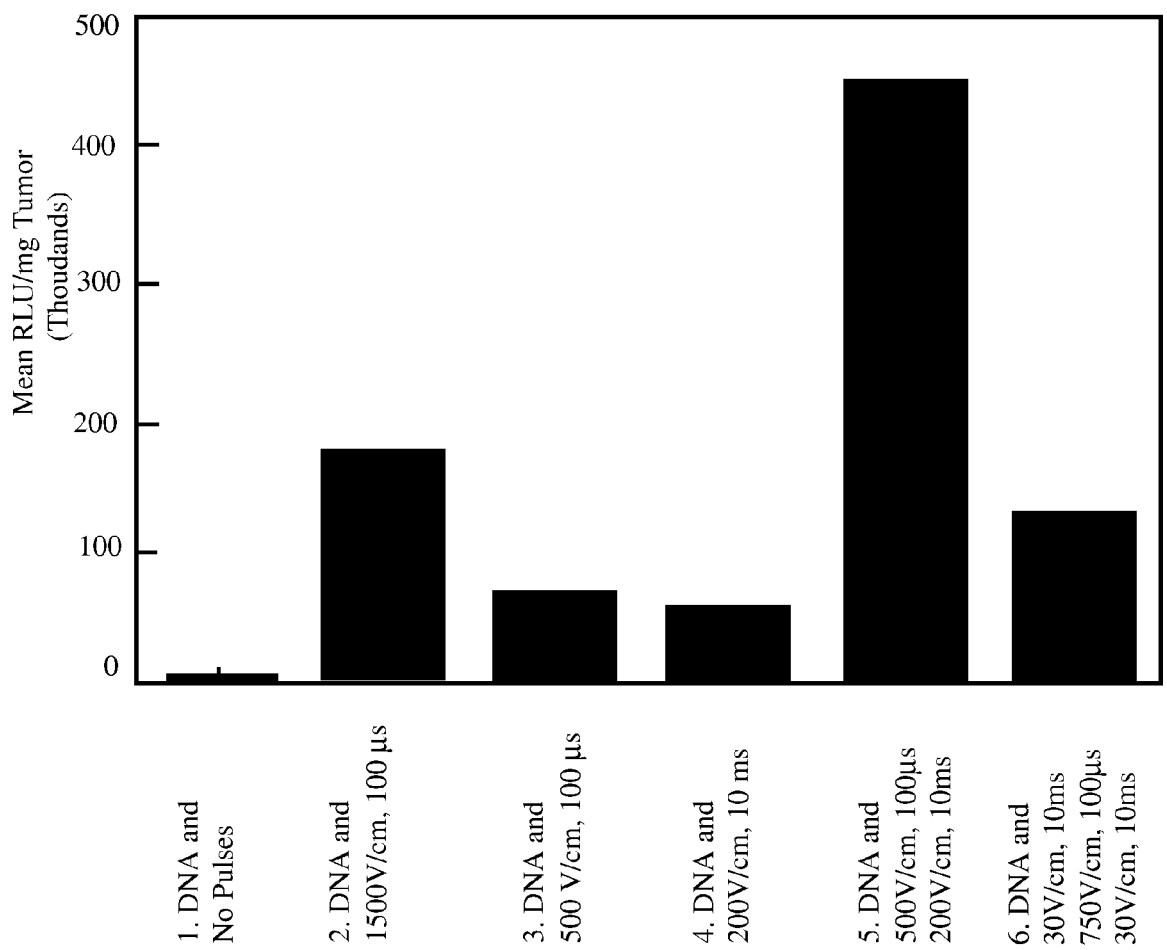
FIG. 6 shows mean quantitative expression data 48 hours after delivering a plasmid coding for the luciferase reported molecule in vivo by application of pulsed fields.

Mean quantitative expression data 48 hours after using electric fields to deliver a plasmid coding for the luciferase reporter molecule in rat hepatocellular carcinomas in vivo are shown in FIG. 6. Traditional syringe and needle injection was used to administer a solution of the plasmid directly into a tumor prior to electrical treatment. Animals in each of the groups (bars) represented in FIG. 6 were treated as follows:

1. DNA and no pulses.
2. DNA followed by 1500 V/cm pulses that were 100 µs in duration (type 2 pulses; the currently used standard).
3. DNA followed by 500 V/cm pulses that were 100 µs in duration (type 2 pulses).
4. DNA followed by 200 V/cm pulses that were 10 ms in duration (type 3 pulses).
5. DNA followed by 500 V/cm pulses that were 100 µs in duration and pulses that were 200 V/cm with a duration of 10 ms (combined type 2 and type 3 pulses).
6. DNA followed by 30 V/cm pulses that were 10 ms in duration, 750 V/cm pulses that were 100 µs in duration, and 30 V/cm pulses that were 10 ms in duration (combined types 1, 2, and 3 pulses).

Luciferase expression for 1500 V/cm pulses of 100 µs duration (2) is the currently accepted standard for delivering molecules in vivo. Higher expression can be obtained even when electroporation pulses with a lower field strength (500 V/cm) were used and combined with 200 V/cm electrophoretic pulses (5). The magnitude of the expression was greater than the sum of the magnitudes of the two components when used alone (3+4). One potential mechanism for this synergy has already been described.

Figure 7A:
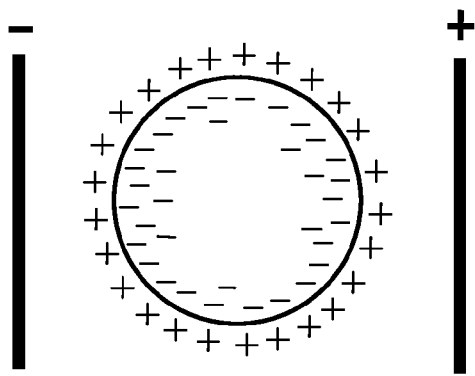
FIGS. 7A-7F illustrate a proposed sequence of events occurring with the combined use of types 1, 2, and 3 pulses.
Figure 7B:
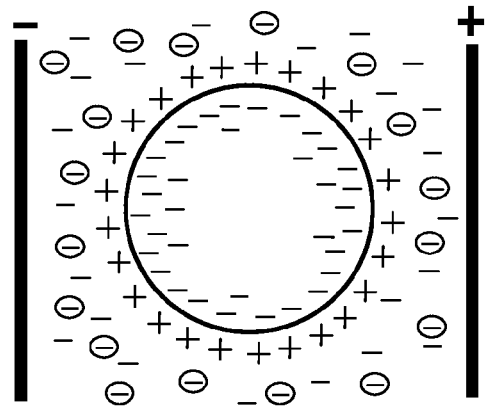
Figure 7C:
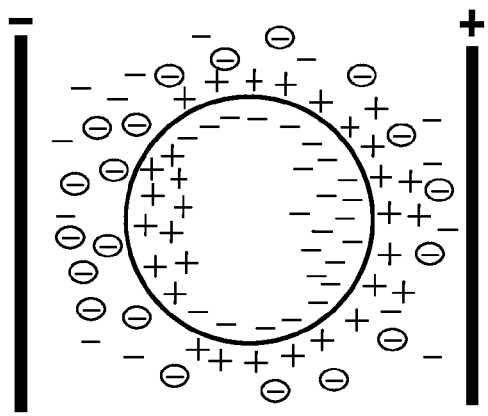

The data for method (6) indicate a result similar to the current standard. A proposed mechanism for this is as follows and is illustrated in FIGS. 7A-7F, although this is not intended as a limitation: A cell with a resting potential in a conductive medium is placed between two electrodes (FIG. 7A). A molecule is introduced into the tissue (FIG. 7B). Pulses of type 1 are applied to electrophoretically distribute DNA throughout the interstitial spaces (FIG. 7C). Since these pulses are insufficient to cause cell membrane electroporation, the applied field induces a polarized state in the cell, which could attract negatively charged DNA molecules to the side of the cell facing the negatively charged electrode. This may cause an electrostatic adhesion of the DNA molecules to the cell membrane, which by proximity would provide a greater chance for DNA to enter the cell after electroporation has been achieved in the next step.

Figure 7D:
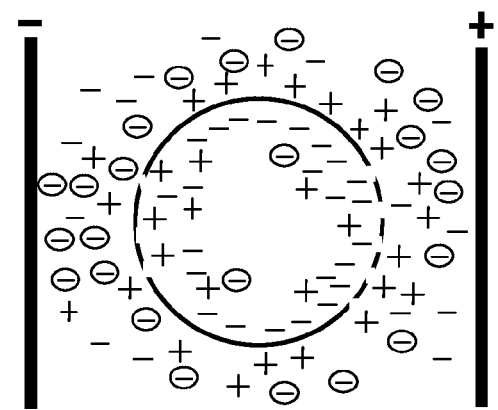
Figure 7E:
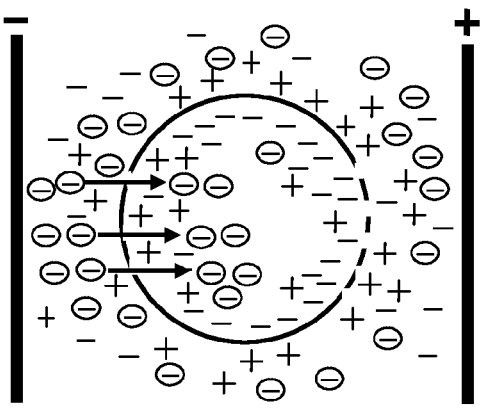

Next type 2 pulses are applied to cause electroporation (FIG. 7D). A rapid depolarization of the cell membrane results, causing an exchange of molecules on either side of the membrane. Pulses of type 3 are then applied (FIG. 7E), causing an electrophoretic movement of the negatively charged molecules through the permeabilized membrane surface facing the negative electrode. Such a movement could potentially introduce more plasmid DNA into each cell, thereby increasing expression.

Figure 7F:
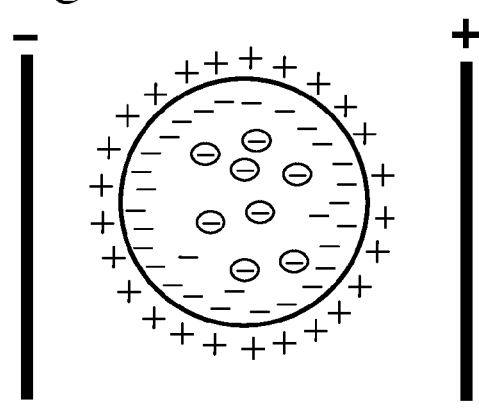

Minutes to hours after pulsation, the cell membrane reseals by normal membrane fluidity, leaving the plasmid DNA inside the cell (FIG. 7F).

Variation in the, Combined Use of Pulse Type 2 and Type 3

The preceding two examples illustrate a combined use of pulse types 2 and 3. In these examples the positive and negative electrodes were in the same physical orientation for both types of administered pulses. An alternate method of applying pulse types 2 and 3 involves switching the orientation of the positive and negative electrodes after type 2 pulses have been administered but before type 3 pulses have been administered.

Figure 8:
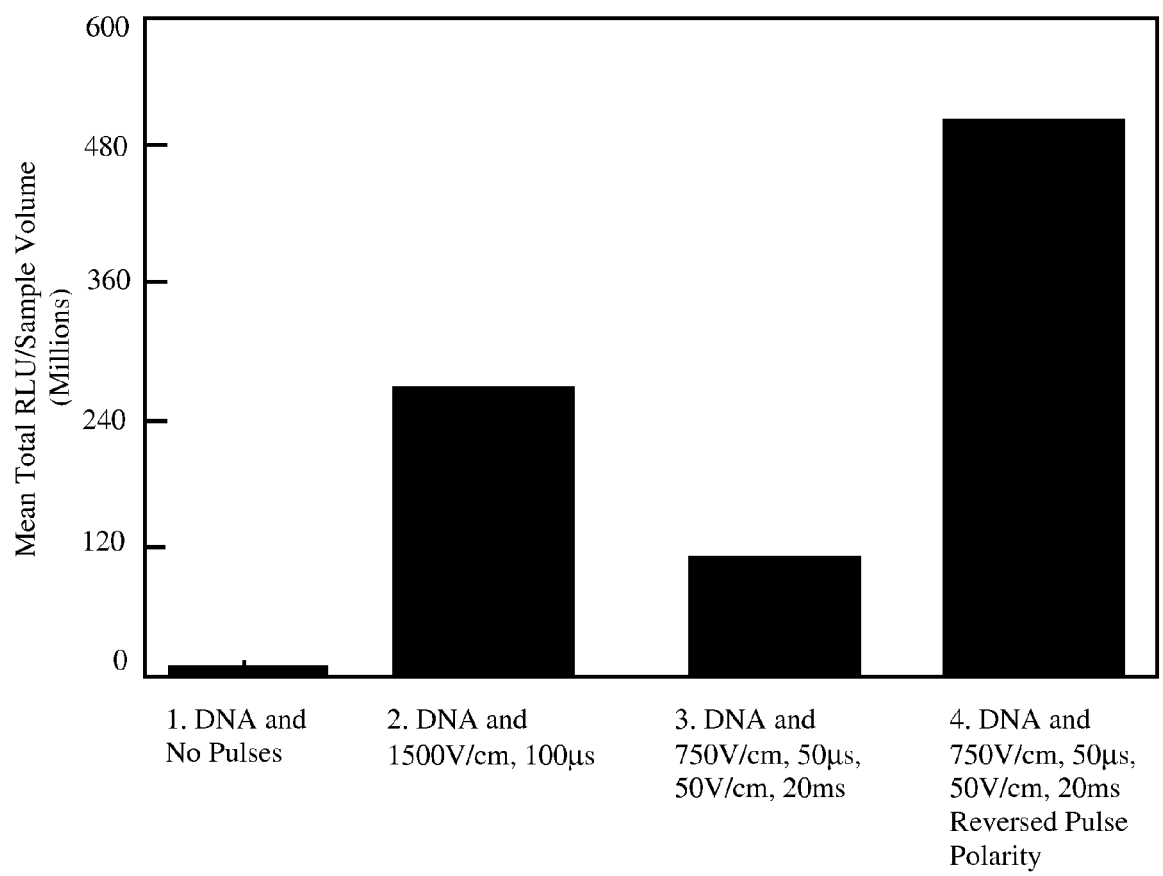
FIG. 8 shows mean quantitative expression data for the luciferase reporter molecule in normal mouse muscle samples 2 days after electrically mediated delivery of plasmid coding for the luciferase cDNA.

FIG. 8 shows mean quantitative expression data for the luciferase reporter molecule in normal mouse muscle samples 2 days after electrically mediated delivery of plasmid coding for the luciferase cDNA. A solution of plasmid DNA was introduced into the muscle tissue by injection prior to electrically treating the muscle in four different manners:

1. DNA and no pulses.
2. DNA followed by 1500 V/cm pulses that were 100 µs in duration (type 2 pulses).
3. DNA followed by 750 V/cm pulses that were 50 µs in duration and 40 V/cm pulses that were 20 ms in duration (combined type 2 and type 3 pulses). These pulses were administered with the same polarity.
4. DNA followed by 750 V/cm pulses that were 50 µs in duration and 40 V/cm pulses that were 20 ms in duration (combined type 2 and type 3 pulses). The type 2 and type 3 pulses were administered with opposite polarity.

The current state of the art is represented by (2), and varying type 2 and type 3 pulses by (3) as in previous examples. The data for (4), however, indicate that changing the polarity further enhances the expression.

Figure 9A:
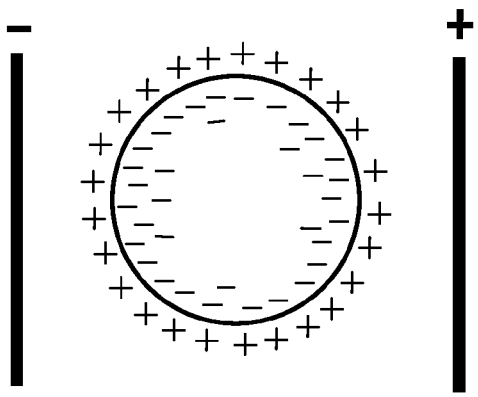
FIGS. 9A-9G represent a proposed mechanism for the use of a type 2 pulse plus alternative administrations of the type 3 pulse with the same or with a reversal of polarity.
Figure 9B:
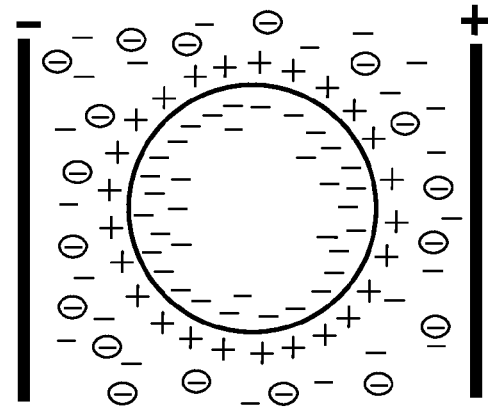
Figure 9C:
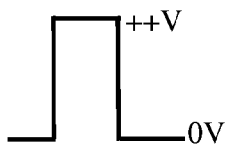

A possible explanation of the phenomenon of this example is as follows and as illustrated in FIGS. 9A-9G, although this is not intended as a limitation:

The cell is placed between two electrodes in a conductive medium (FIG. 9A). A molecule is introduced into the tissue (FIG. 9B). Type 2 pulses are applied to cause electroporation (FIG. 9C). A rapid depolarization of the cell membrane results, causing an exchange of molecules on either side of the membrane.

Figure 9D:
Figure 9B:
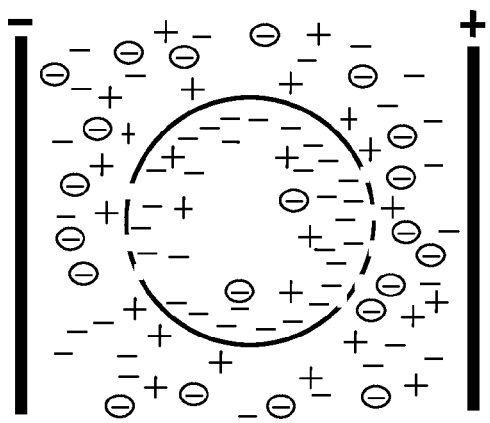
Figure 9B:
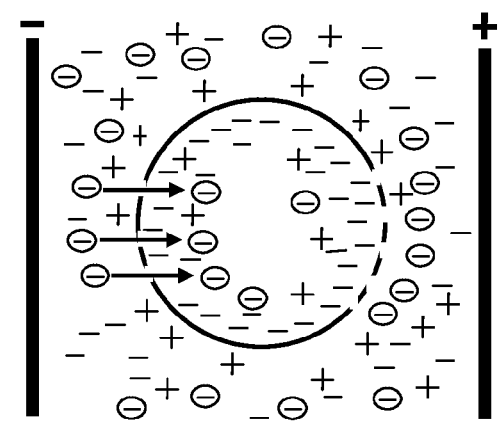
Figure 9E:
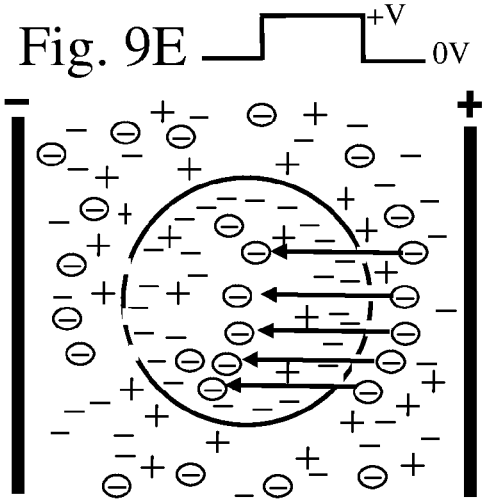

Type 3 pulses are applied to cause an electrophoretic movement of the negatively charged molecules through the permeabilized membrane surface facing the negative electrode as in (3) above (FIG. 9D). Alternatively, as in (4) above, the polarity of the type 3 pulses is opposite (FIG. 9E). This causes electrophoretic movement of the negatively charged DNA molecules through the opposite side of the cell. This opposite side is preferentially more permeabilized when type 2 pulses are applied. An advantage to applying type 3 pulses in this manner is that the desired molecule, such as a DNA molecule, may be electrophoretically moved through an area of membrane that is more permeabilized, which would result in more mass transport than if the type 2 and type 3 pulses were applied with the same polarity.

Figure 9F:
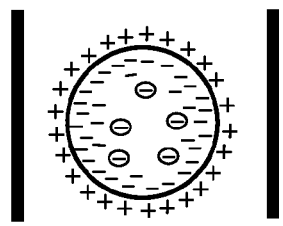
Figure 9G:
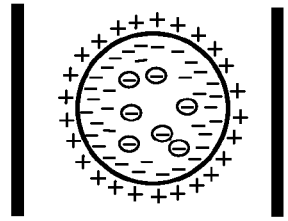

Minutes to hours after pulsation, the cell membrane reseals by normal membrane fluidity, leaving the plasmid DNA inside the cell (FIG. 9F). Potentially, more DNA is transferred by switching polarity between types 2 and 3 pulses to drive the molecules through the side of the cell that has been porated to a greater extent (FIG. 9G).

Figure 10:
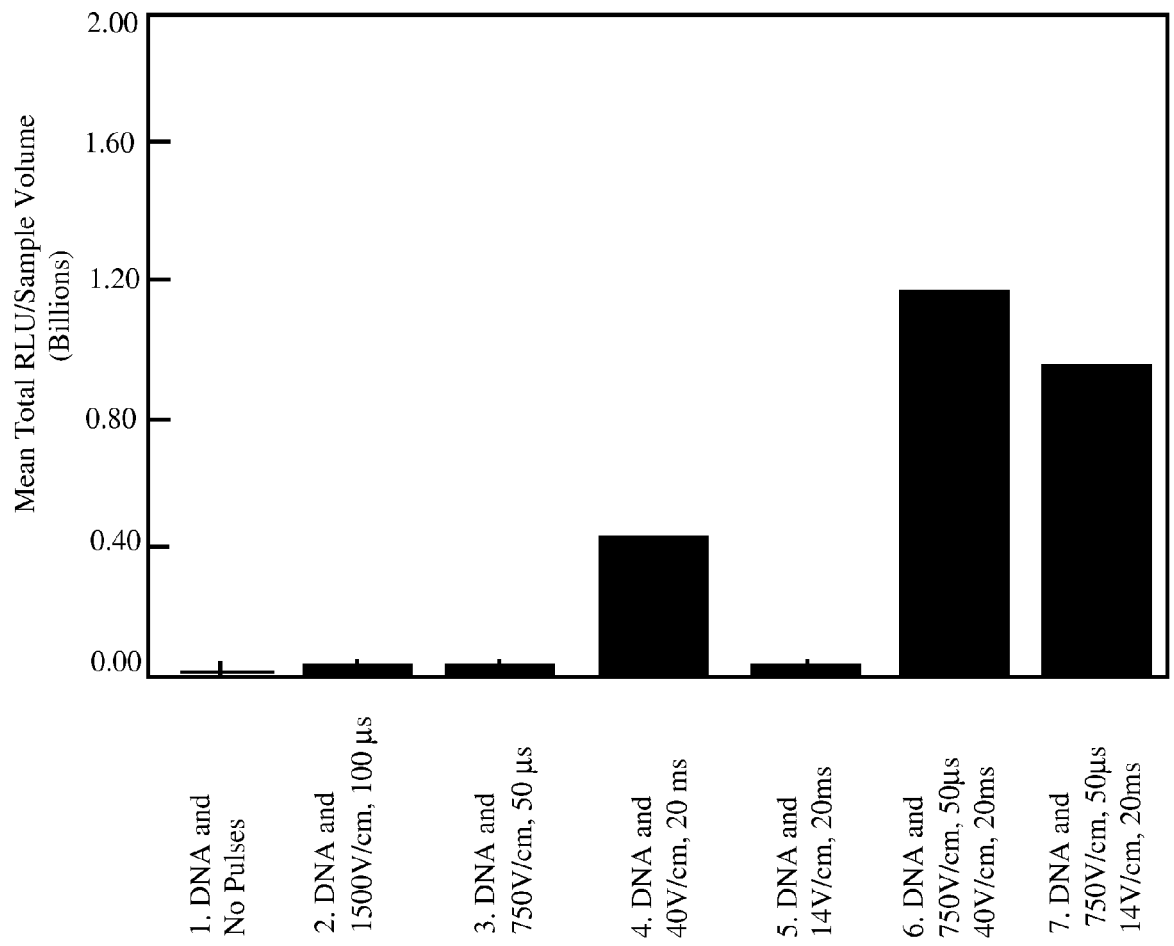
FIG. 10 shows mean quantitative expression data for the luciferase reporter molecule in normal mouse muscle samples 7 days after electrically mediated delivery of plasmid coding for the luciferase cDNA, with the use of varied waveforms for the type 3 pulse.
Figure 11:
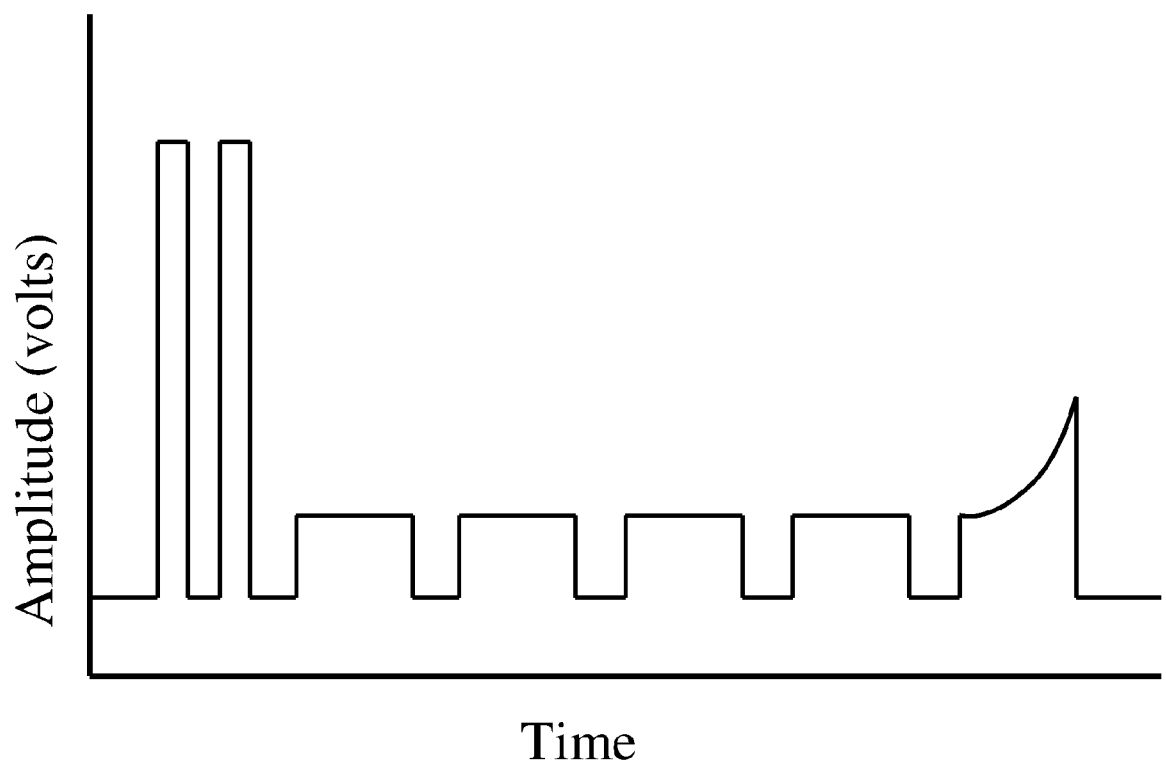
FIG. 11 plots the waveforms of the pulses used for a delivery experiment in which the type 2 pulses were rectangular, but the fifth type 3 pulse contained an exponentially rising component in the latter stages of the pulse.

Variation of the Waveform Used for Type 3 Pulses During the Combined Use of Types 2 and 3 Pulses Mean quantitative expression data for the luciferase reporter molecule in normal mouse muscle samples 7 days after electrically mediated delivery of plasmid coding for the luciferase cDNA are shown in FIG. 10. Samples were treated in eight different manners:

1. DNA and no pulses.
2. DNA followed by 1500 V/cm pulses that were 100 µs in duration (type 2 pulses).
3. DNA followed by 750 V/cm pulses that were 50 µs in duration (type 2 pulses).
4. DNA followed by 40 V/cm pulses that were 20 ms in duration (type 3 pulses).
5. DNA followed by 14 V/cm pulses that were 20 ms in duration (type 3 pulses).
6. DNA followed by 750 V/cm pulses that were 50 µs in duration and pulses that were 40 V/cm with a duration of 20 ms (combined types 2 and 3 pulses).
7. DNA followed by 750 V/cm pulses that were 50 µs in duration and pulses that were 14 V/cm with a duration of 14 ms (combined types 2 and 3 pulses).

Two type 2 pulses, in series, were delivered for each of the treatment conditions that used the type of pulses above. Five type 3 pulses were delivered in series for those treatment conditions that used type 3 pulses. The difference between this example and the three previous ones was in the waveform of the pulses. Whereas in the previous examples rectangular pulses were used for both types 2 and 3 pulses, here the type 2 pulses were rectangular, but the fifth type 3 pulse contained an exponentially rising component in the latter stages of the pulse indicated in FIG. 11.

The results of this example indicate that combining type 2 and type 3 pulses causes an increase in luciferase expression in muscle samples relative to the sum of the expression from the samples that received either type 2 or type 3 pulses alone. A possible explanation for this synergistic effect is similar, to that given above, except that the waveform for the postelectroporation electrophoresis is different, indicating that alternative waveforms to the rectangular shape can be beneficial for this type of delivery.

Combined Use of Type 1 and Type 2 Pulses

Figure 12:
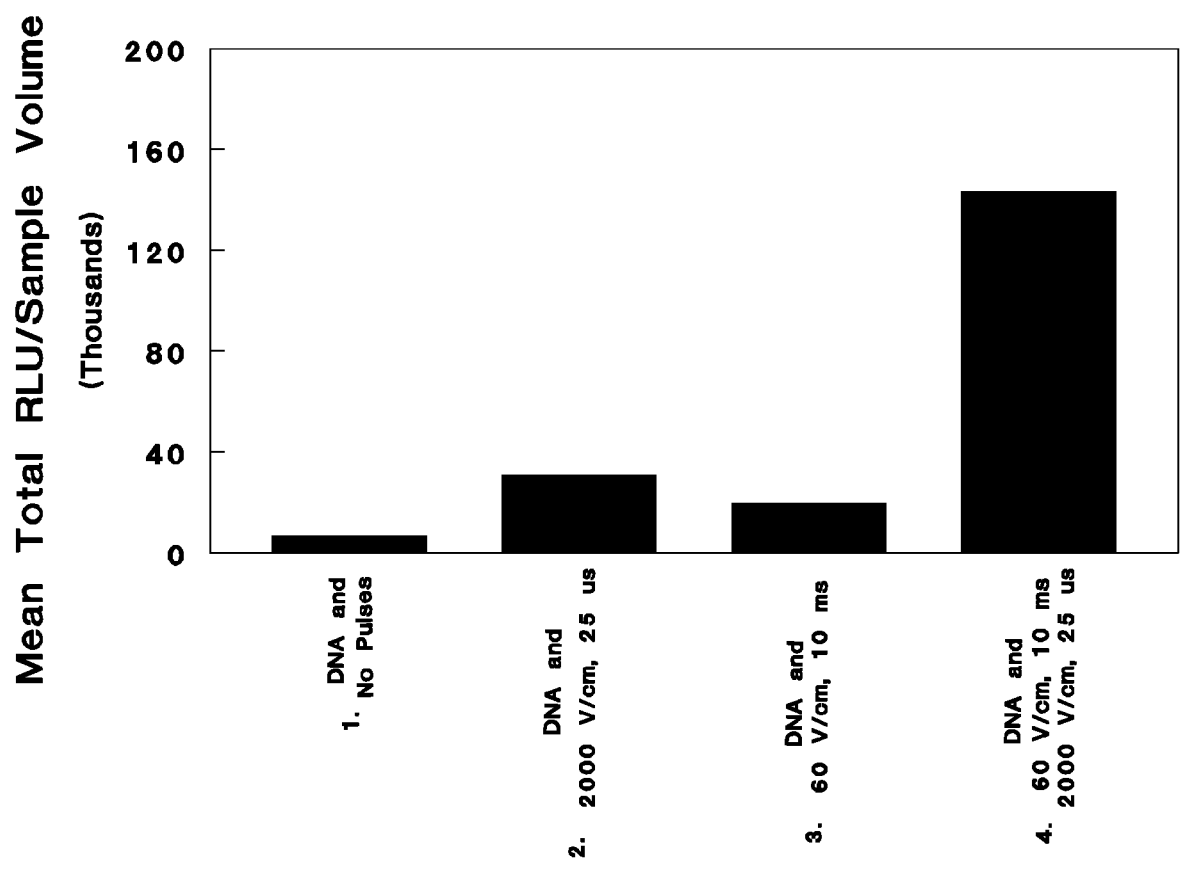
FIG. 12 shows mean quantitative expression data for the luciferase reporter molecule in normal mouse muscle samples 48 h after electrically mediated delivery of plasmid coding for the luciferase cDNA, with the use of sequential type 1 and type 2 pulses.
Figure 13:
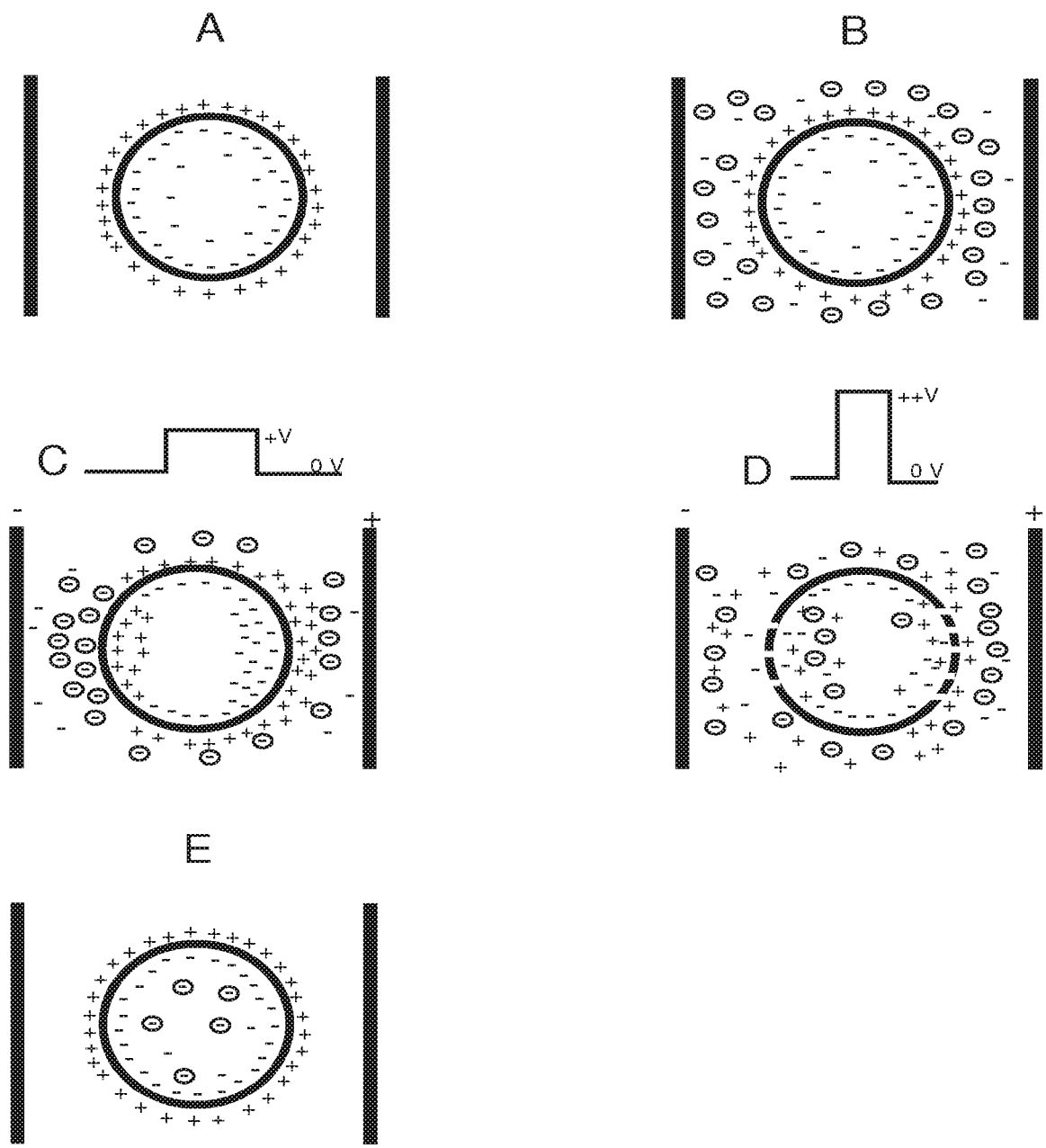
FIGS. 13A-13E represent a proposed mechanism for the use of a type 1 pulse followed by a type 2 pulse.

Mean quantitative expression data for the luciferase reporter molecule in normal mouse muscle samples 48 h after electrically mediated delivery of plasmid coding for the luciferase cDNA are shown in FIG. 12. Samples were treated in four different manners:

1. DNA and no pulses.
2. DNA followed by 2000 V/cm pulses that were 25 µs in duration (type 1 pulses).
3. DNA followed by 60 V/cm pulses that were 10 ms in duration (type 2 pulses).
4. DNA followed by 60 V/cm pulses that were 10 ms in duration (type 1 pulses) and 2000 V/cm pulses that were 25 µs in duration (combined types 1 and 2 pulses).

Luciferase expression for (4), which utilized combined types 1 and 2 pulses, was higher than (2) and (3), which utilized a single type of pulse. In addition, expression for (4) was higher than the sum of the expression levels of (2) and (3).

These data indicate that using type 1 pulses with the traditional pulses used for electroporation (type 2) can augment the resulting expression. It is believed that the combined use of types 1 and 2 pulses has not yet been optimized, and that additional synergy may result in an optimization of the augmenting effect of the combined pulses.

A potential mechanism for this effect is depicted in FIGS. 13A-13E. In FIG. 13A, a cell with a resting potential is placed in a conductive medium between two electrodes. A molecule is then introduced into the tissue (FIG. 13B), here plasmid DNA, which is negatively charged in solution.

Next pulses of type 1 are applied to electrophoretically distribute the DNA throughout the interstitial space (FIG. 13C). Since this pulse is not sufficient to cause cell membrane electroporation, the applied field induces a polarized state in the cell, attracting negatively charged molecules to the side of the cell facing the negatively charged electrode. Electrostatic adhesion of the molecules to the cell membrane is caused, enhancing the molecule's proximity to the membrane and hence its chance for entry following the subsequent electroporation step.

Pulses of type 2 are applied to cause electroporation (FIG. 13D). A rapid depolarization of the cell membrane results, causing an exchange of molecules on either side of the membrane. Minutes to hours after pulsation, the cell membrane reseals by normal membrane fluidity, leaving the molecule inside the cell (FIG. 1 3E).

It may be appreciated by one skilled in the art that additional embodiments may be contemplated, including alternate waveforms and pulsing sequences.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained theeby the new and useful constructions, and reasonable mechanical equivalents thereof obvious to those skilled in the art, are set forth in the appended claims.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. A method for delivering a charged molecule into a cell in vivo comprising the steps of:
    positioning a charged molecule outside and generally adjacent to the cell in vivo, wherein the cell comprises a constituent of a tissue;
    delivering a first electromagnetic pulse to the cell having a strength and duration sufficient to cause electroporation of the cell; and
    delivering a second electromagnetic pulse to the cell having a strength and duration insufficient to cause electroporation of the cell and sufficient to cause an electromigration of the molecule toward and into the cell, wherein at least one of the first pulse and the second pulse comprises an exponentially rising component.

2. The method recited in claim 1, wherein the molecule positioning step comprises the step of delivering the molecule into an interstitial space adjacent the cell.

3. The method recited in claim 1, further comprising the step of placing a pair of electrodes with opposite polarity adjacent the tissue and in spaced-apart relation from each other, and wherein the pulse delivering steps comprise administering the pulses via the electrode pair.

4. The method recited in claim 3, further comprising the step of delivering a third electromagnetic pulse prior to the first pulse, the third pulse having a strength and duration insufficient to cause electroporation of the cell and sufficient to cause an electromigration of the molecule toward the cell, wherein at least one of the first pulse, the second pulse and the third pulse comprises an exponentially rising field strength component.

5. The method recited in claim 3, wherein during delivery of the first pulse a first of the electrode pair has a first polarity and a second of the electrode pair has a second polarity opposite the first polarity and during delivery of the second pulse the first electrode has the second polarity and the second electrode has the first polarity.

6. The method recited in claim 1, wherein the second pulse has a field strength in a range of 1 to 2000 V/cm.

7. The method recited in claim 1, wherein the first pulse has a field strength in a range of 50 to 10,000 V/cm.

8. The method recited in claim 7, wherein the first pulse has a duration of at least 1 μs.

9. The method recited in claim 1, wherein at least one of the first and the second pulse comprises a series of pulses.

10. The method recited in claim 1, wherein the first pulse is delivered with a first polarity and the second pulse is delivered with a second polarity opposite the first polarity.

11. The method recited in claim 1, wherein the charged molecule positioning step comprises a step selected from the group consisting of injection, particle bombardment, and jet injection.

12. The method recited in claim 1, wherein the charged molecule comprises a plurality of different charged molecules.

* * * * *